(12) United States Patent
Avinash et al.

(10) Patent No.: US 9,514,250 B2
(45) Date of Patent: Dec. 6, 2016

(54) SYSTEM AND METHOD FOR ANALYZING AND VISUALIZING ENUMERATED INFORMATION

(75) Inventors: Gopal Biligeri Avinash, Menomonee Falls, WI (US); Eric David Kiger Garland, Glen Burnie, MD (US); Ananth P. Mohan, Waukesha, WI (US)

(73) Assignee: General Electric Company, Schenectady, NY (US)

(*) Notice: Subject to any disclaimer, the term of this patent is extended or adjusted under 35 U.S.C. 154(b) by 1521 days.

(21) Appl. No.: 12/845,853

(22) Filed: Jul. 29, 2010

(65) Prior Publication Data

US 2012/0030217 A1   Feb. 2, 2012

(51) Int. Cl.
*G06F 17/30* (2006.01)
*G06F 7/00* (2006.01)
*G06Q 50/24* (2012.01)
*G06F 19/00* (2011.01)

(52) U.S. Cl.
CPC ... *G06F 17/30994* (2013.01); *G06F 17/30985* (2013.01); *G06F 19/322* (2013.01); *G06F 19/324* (2013.01)

(58) Field of Classification Search
USPC ....... 707/636, 696, 706, 711, 715, 728, 732, 707/736–749, 781, 805, 814, 830
See application file for complete search history.

(56) References Cited

U.S. PATENT DOCUMENTS

| | | | |
|---|---|---|---|
| 2003/0190602 A1* | 10/2003 | Pressman et al. | 435/5 |
| 2006/0287890 A1* | 12/2006 | Stead et al. | 705/3 |
| 2007/0134688 A1* | 6/2007 | Symmans et al. | 435/6 |
| 2009/0138279 A1 | 5/2009 | Avinash et al. | |
| 2009/0290772 A1 | 11/2009 | Avinash et al. | |
| 2009/0292478 A1 | 11/2009 | Avinash et al. | |
| 2009/0292551 A1 | 11/2009 | Sirohey et al. | |
| 2009/0292557 A1 | 11/2009 | Sirohey et al. | |
| 2011/0212090 A1* | 9/2011 | Pedersen et al. | 424/133.1 |
| 2012/0124051 A1* | 5/2012 | Lin | G06F 17/30734 707/739 |

* cited by examiner

*Primary Examiner* — Sangwoo Ahn (57) ABSTRACT

A system and method for analyzing clinical data includes a reference database comprising a stored set of reference data comprising enumerated results of a reference population for a clinical test. The system also includes a patient database comprising a stored set of clinical data corresponding to a patient result for the clinical test that is selected from the enumerated results. A processor is included in the system and is programmed to access the patient and reference databases, identify a distribution of reference data over the enumerated test results, and calculate a relevance index based on the distribution of reference data. The processor is further programmed to compare the patient result to the distribution of reference data, calculate a disagreement index based on the comparison, and calculate a deviation index from the relevance and disagreement indices. A graphical user interface is also included to output a visualization of the deviation index.

20 Claims, 9 Drawing Sheets

SYSTEM AND METHOD FOR ANALYZING AND VISUALIZING ENUMERATED INFORMATION

BACKGROUND OF THE INVENTION

Embodiments of the invention relate generally to diagnostic imaging and, more particularly, to a system and method for analyzing and visualizing enumerated information.

Clinical information regarding a patient is often collected and stored in an enumerated format, such as a binary format, for example. Binary clinical data is typically viewed by healthcare professionals in a tabular format, as illustrated in Table 1. While such a method of display appears straightforward, many drawbacks are inherent in the simplicity of the display method.

TABLE 1

| Prior Art Display of Test Results | | |
| --- | --- | --- |
| Clinical Test | Response | Response Key |
| Image Test 1 | Y | Y = Yes; N = No; –4 = Not Available |
| Image Test 2 | N | Y = Yes; N = No; –4 = Not Available |
| Image Test 3 | Y | Y = Yes; N = No; –4 = Not Available |
| Image Test 4 | Y | Y = Yes; N = No; –4 = Not Available |
| Image Test 5 | Y | Y = Yes; N = No; –4 = Not Available |
| Clinical Response Test 1 | N | Y = Yes; N = No; –4 = Not Available |
| Clinical Response Test 2 | N | Y = Yes; N = No; –4 = Not Available |
| Clinical Response Test 3 | Y | Y = Yes; N = No; –4 = Not Available |
| Clinical Response Test 4 | Y | Y = Yes; N = No; –4 = Not Available |

As illustrated in Table 1, a tabular display of binary data illustrates little importance of the data. As such, the tabular display may obscure the importance and relevance of a particular test result. Unless a healthcare or other professional viewing the data knows what each test is designed for and what each response corresponds to, the data is essentially meaningless.

Also, with the networking of medical devices, healthcare professionals have access to test results that may not fall within their area of expertise. While it may be possible for a healthcare professional to understand the meaning of all types of test results, such understanding takes time and experience. For example, sometimes the "good" or "normal" response to one binary question is "Yes" while the "good" response to another binary question is "No." A healthcare professional typically learns this information over years of experience.

Further, the amount of data that a healthcare professional has available continues to increase, the size of spreadsheets containing the binary data increases and it becomes increasingly difficult for healthcare professionals to distinguish trends or patterns in the binary data. A tabular display of binary data does not typically provide any indication of the significance of the data or indicate whether the clinical data is consistent with a reference baseline. That is, the tabular display may not provide any indication of whether a patient's clinical data deviates from the norm.

Accordingly, there is a need to present enumerated data to a user in a manner that allows the user to quickly glean information from the data, understand the relative significance of a multitude of enumerated results, and correlate the results with a reference.

Therefore, it would be desirable to design a system and method analyzing and visualizing enumerated clinical data that overcome the aforementioned drawbacks.

BRIEF DESCRIPTION OF THE INVENTION

In accordance with one aspect of the invention, a system for analyzing clinical data includes a reference database having stored thereon a set of reference data comprising a plurality of enumerated results of a reference population for a clinical test and a patient database having stored thereon a set of clinical data corresponding to a patient result for the clinical test, wherein the patient result is selected from the plurality of enumerated results. The system also includes a processor programmed to access the patient database and the reference database, identify a distribution of the reference data over the plurality of enumerated test results, and calculate a relevance index based on the distribution of the reference data. The processor is further programmed to compare the patient result to the distribution of the reference data, calculate a disagreement index based on the comparison, and calculate a deviation index from the relevance index and the disagreement index. The system further includes a graphical user interface (GUI) configured to output a visualization of the deviation index to a user.

In accordance with another aspect of the invention, a method includes accessing a first dataset comprising results from a clinical test having a plurality of possible outcomes corresponding thereto, the first dataset acquired from a reference population, calculating a reference index from the first dataset, the reference index representing a distribution of the first dataset over the plurality of possible outcomes, and accessing a second dataset comprising an outcome of the plurality of possible outcomes from the clinical test, the second dataset acquired from a patient of interest. The method also includes calculating a patient index from the second dataset, the patient index representing a disagreement between the patient outcome and the distribution of the first dataset, calculating a deviation score based on the reference index and the patient index, and outputting a visualization of the deviation score, the visualization depicting a relevance of the outcome of the second dataset.

In accordance with another aspect of the invention, a computer readable storage medium has stored thereon a computer program comprising instructions, which, when executed by a computer, cause the computer to access a reference dataset comprising results of a reference population for a plurality of clinical tests, each clinical test having a finite number of possible results corresponding thereto. The instructions also cause the computer to access a patient dataset comprising results of a patient of interest for the plurality of clinical tests, the results of the patient of interest selected from the finite number of possible results and calculate a plurality of relevance indices from the reference dataset for the plurality of clinical tests, each of the plurality of relevance indices representing a distribution of the reference dataset for a respective clinical test. Further, the instructions cause the computer to calculate a plurality of disagreement indices, each of the plurality of disagreement indices representing a disagreement between the patient dataset and the reference dataset for a respective clinical test, calculate a plurality of deviation scores based on the plurality of relevance indices and the plurality of disagreement indices, and output a graphical display of the plurality of deviation scores, the graphical display depicting a relevance of the results of the patient of interest with respect to the reference population.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Figure 1:
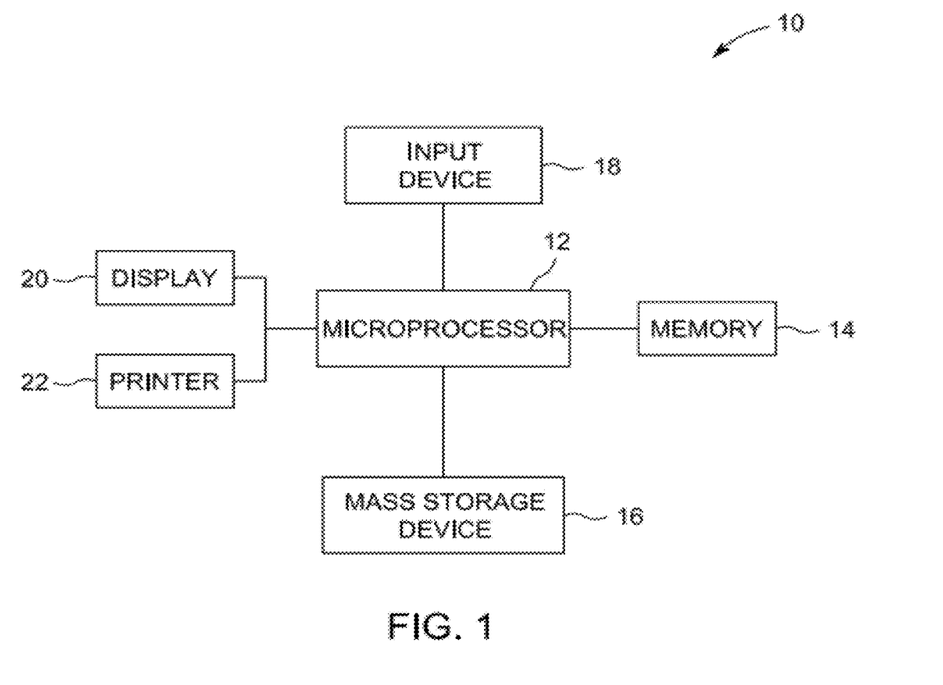
FIG. 1 is a block diagram of an exemplary processor-based device or system in accordance with one embodiment of the present invention.

Referring first to FIG. 1, an exemplary processor-based system 10 for use in conjunction with the present technique is depicted. In one embodiment, exemplary processor-based system 10 is a general-purpose computer, such as a personal computer, configured to run a variety of software, including software implementing all or part of the presently disclosed techniques, including the methods and functionality described throughout the instant disclosure. Alternatively, in other embodiments, processor-based system 10 may comprise, among other things, a mainframe computer, a distributed computing system, or an application-specific computer or workstation configured to implement all or part of the present techniques based on specialized software and/or hardware provided as part of the system. Further, processor-based system 10 may include either a single processor or a plurality of processors to facilitate implementation of the presently disclosed functionality.

In general, exemplary processor-based system 10 includes a microcontroller or microprocessor 12, such as a central processing unit (CPU), which executes various routines and processing functions of system 10. For example, microprocessor 12 may execute various operating system instructions as well as software routines configured to effect certain processes stored in or provided by a manufacture including a computer readable-medium, such as a memory 14 (e.g., a random access memory (RAM) of a personal computer) or one or more mass storage devices 16 (e.g., an internal or external hard drive, a solid-state storage device, CD-ROM, DVD, or other storage device). In addition, microprocessor 12 processes data provided as inputs for various routines or software programs, such as data provided in conjunction with the present techniques in computer-based implementations.

As described in more detail below, system 10 accesses clinical data acquired from a patient as well as standardized reference data corresponding to a reference population of interest. In various embodiments, the clinical data may include enumerated results acquired from clinical tests, patient monitors, imaging systems of various modalities, computers, or any other suitable systems capable of collecting or receiving data regarding a patient.

Such data may be stored in, or provided by, memory 14 or mass storage device 16. Alternatively, such data may be provided to microprocessor 12 via one or more input devices 18. As will be appreciated by those of ordinary skill in the art, input devices 18 may include manual input devices, such as a keyboard, a mouse, or the like. In addition, input devices 18 may include a network device, such as a wired or wireless Ethernet card, a wireless network adapter, or any of various ports or devices configured to facilitate communication with other devices via any suitable communications network, such as a local area network or the Internet. Through such a network device, system 10 may exchange data and communicate with other networked electronic systems, whether proximate to or remote from system 10. It will be appreciated that the network may include various components that facilitate communication, including switches, routers, servers or other computers, network adapters, communications cables, and so forth.

Results generated by microprocessor 12, such as the results obtained by processing data in accordance with one or more stored routines, may be stored in memory device 14, may undergo additional processing, or may be provided to an operator via one or more output devices, such as a display 20 and/or a printer 22. Also, based on the displayed or printed output, an operator may request additional or alternative processing or provide additional or alternative data, such as via input device 18. As will be appreciated by those of ordinary skill in the art, communication between the various components of processor-based system 10 may typically be accomplished via a chipset and one or more busses or interconnects which electrically connect the components of system 10. Notably, in certain embodiments of the present techniques, processor-based system 10 may be configured to facilitate patient diagnosis, as discussed in greater detail below.

Figure 2:
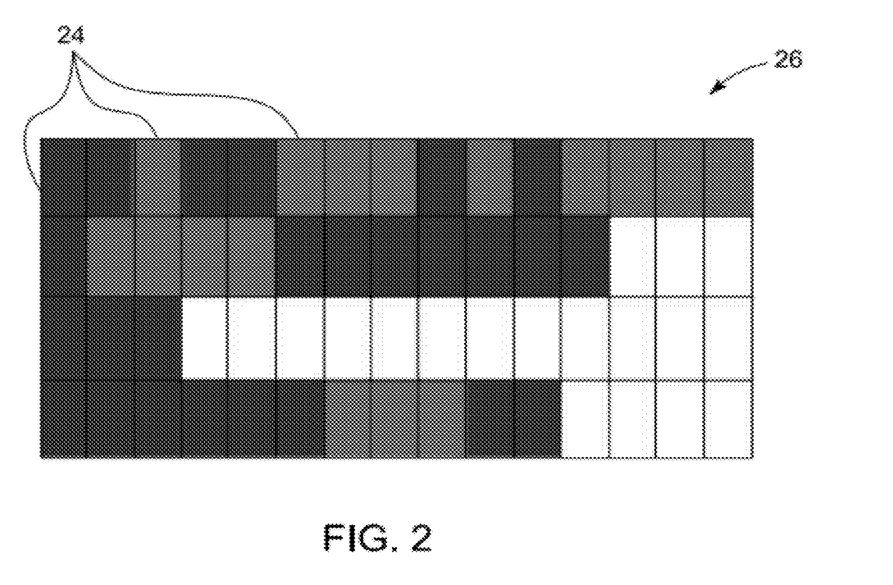
FIG. 2 illustrates a dual color graphical view representing enumerated clinical data in Table 2.

Table 2, below, illustrates an exemplary patient data set comprising patient responses for a number of different tests. As shown in FIG. 2, such patient responses may be displayed as individual cells 24 in a grid 26, where one answer is represented as a first color (e.g., False=black) and another answer is represented as a second color (e.g., True=white). However, while such a visualization may simplify the presentation of the patent test result data for a clinician, it may not provide a desired indication to the clinician of whether the patient's response is significant or not. For example, the visualization of patient responses in grid 26 does not indicate whether a given patient response is consistent with a reference baseline or expected response.

TABLE 2

Tabular View of Binary Test Results

| Test 1 | Response | Test 2 | Response | Test 3 | Response | Test 4 | Response |
|---|---|---|---|---|---|---|---|
| Q1 | True | Q1 | True | Q1 | True | Q1 | True |
| Q2 | True | Q2 | False | Q2 | True | Q2 | True |
| Q3 | False | Q3 | False | Q3 | True | Q3 | True |
| Q4 | True | Q4 | False | | | Q4 | True |
| Q5 | True | Q5 | False | | | Q5 | True |
| Q6 | False | Q6 | True | | | Q6 | True |
| Q7 | False | Q7 | True | | | Q7 | False |
| Q8 | False | Q8 | True | | | Q8 | False |
| Q9 | True | Q9 | True | | | Q9 | False |
| Q10 | False | Q10 | True | | | Q10 | True |
| Q11 | True | Q11 | True | | | Q11 | True |
| Q12 | False | Q12 | True | | | | |
| Q13 | False | | | | | | |
| Q14 | False | | | | | | |
| Q15 | False | | | | | | |

Figure 3:
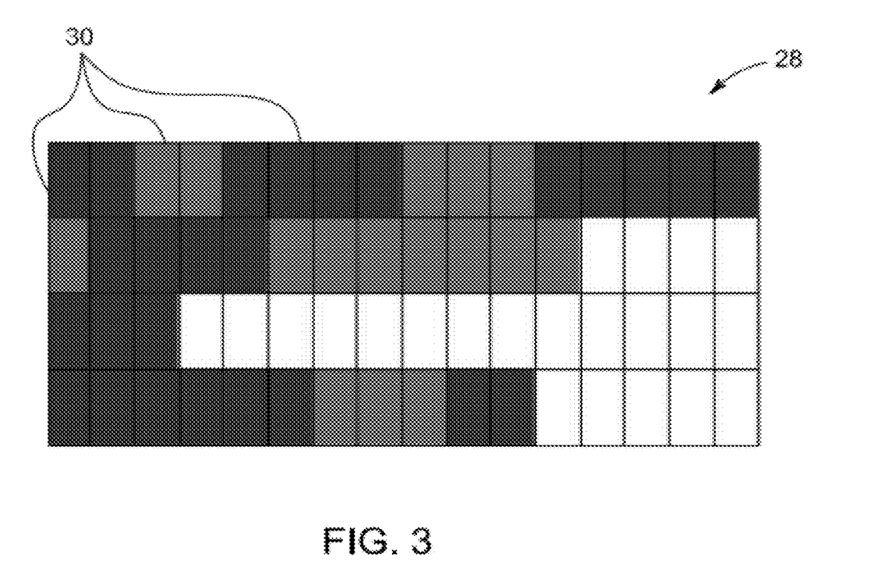
FIG. 3 illustrates a dual color graphical view representing agreement of the enumerated clinical data in Table 2 with a reference population.

Referring to FIG. 3, the exemplary test result data of Table 2 is displayed in a grid 28 using an alternative format. Specifically, cells 30 corresponding to each patient response are color-coded according to whether the patient's response is in agreement with the majority of a reference population. Thus, a patient response that is in agreement with the majority is coded using a first color (e.g., black) and a patient response that is not in agreement with the majority is coded using a second color (e.g., gray).

Figure 4:
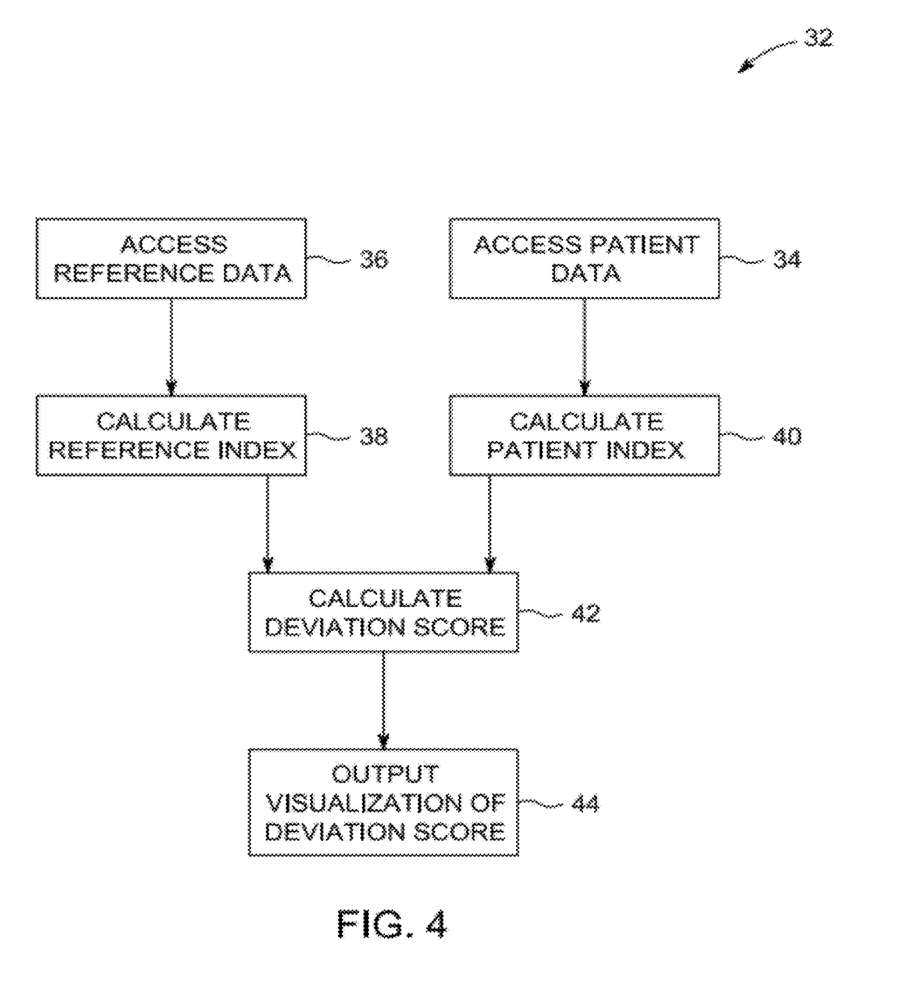
FIG. 4 illustrates a technique for generating a visual display of the relevance of enumerated clinical information in accordance with one embodiment of the present invention.

Referring now to FIG. 4, a technique 32 is set forth for generating an alternative visual display of the relevance of enumerated clinical information. As described in detail below, technique 32 visualizes a patient's response to a clinical test in a manner that gives meaning to the patient's response in terms of the normal response of the reference population.

Technique 32 begins by accessing clinical patient data at step 34. The patient data may be any type of enumerated clinical data, such as test results corresponding to a clinical test having a finite number of possible results. According to one embodiment, the patient data is one or more patient responses for a given binary test or series of binary tests. For example, patient data may indicate that the patient responded "Yes" to a given Yes/No question on a medical questionnaire. Alternatively, the patient data is a patient response for a test having more than two possible results, such as, for example, a blood type test. As another example, the patient data represents a patient-related response to a question having a finite number of possible responses, each indicating a level of agreement or disagreement with the question. For example, the patient data may be a clinician's answer to the question "How dependent is the patient on help?" selected from the following possible answers: (1) Not at all dependent; (2) Somewhat dependent; (3) Somewhat independent; (4) Independent.

At step 36, a set of standardized reference data is accessed. The standardized reference data is selected to correspond to the same type of clinical test as patient data. In some embodiments, standardized reference data may be generated from other persons or groups of persons. For example, standardized reference data for a given test may be compiled from tests performed on persons deemed to have normal health and persons diagnosed with certain diseases, such as Alzheimer's disease (AD) or Parkinson's disease (PD), for example. Further, a subset of the standardized reference data may be selected based on a demographic characteristic, such as the race, gender, or age of the persons from which the data was collected. For example, if a patient is a sixty-five-year-old woman, a subset of the standardized reference data grouped to include clinical test results pertaining to women between sixty and seventy years of age may be more relevant for comparative purposes than a group of standardized reference data composed of data collected from men between twenty and thirty years of age.

Once the standardized reference data is accessed, a reference index or relevance index, RI, is calculated at step 38 to represent the relevance of the particular clinical test. The relevance index identifies each of the possible results of a given test, assigns each test result to a respective enumerated bin, and determines the relative percentages, $x(1):x(n)$, of the reference data for each enumerated bin. The maximum percentage (x_max) and minimum percentage (x_min) are identified for the set of enumerated bins. Using the calculated maximum and minimum percentages, technique 32 calculates the relevance index, RI, according to:

$$RI = (max\_R - min\_R) \qquad \text{Eqn. 1,}$$

where $$max\_R = \frac{x\_max}{x\_max} \text{ and } min\_R = \frac{x\_min}{x\_max}.$$

For a completely relevant (i.e., ideal) test, each response in the reference population would correspond to the same bin. Thus, max_R=1, min_R=0, and RI=1. For a completely irrelevant test, the relative percentages of all bins are equal. Thus, max_R=1, min_R=1, and RI=0. All other tests have a relevance index between zero and one, with higher relevance indices indicating a more useful test.

At step 40, a patient index or disagreement index, DI, is calculated to indicate of the relevance of the particular bin that the patient's test result is in. The disagreement index is calculated based on the patient's test result and the relative probability, P(i), for the corresponding bin according to:

$$P(i) = \frac{x(i) * 100}{[x(1) + x(2) + \ldots + x(n)]}, \qquad \text{Eqn. 2}$$

where x(i) represents the relative percentage of the enumerated bin corresponding to the patient's test result. For example, if the patient's test result corresponds to bin 2, technique 32 references the corresponding relative percentage for bin 2, x(2), calculated from the reference data.

The disagreement index, DI, for a test result is calculated according to $$DI(i) = (1 - P(i)) \qquad \text{Eqn. 3.}$$

The disagreement index is defined by values between zero and one and represents the relevance of the particular bin that the patient's result is in. A disagreement index of zero indicates that the entire reference population exhibited the same bin value as the patient; a disagreement index of one indicates no one in the reference population exhibited the same bin value as the patient. Accordingly, where the reference population is selected from a group of normals, the closer the disagreement index is to one, the more abnormal the patient's test result.

At step 42, technique 32 uses the calculated relevance index, RI, and the calculated disagreement index, DI, to calculate a deviation score, DS, for a given test result according to $$DS(i)=RI*DI(i) \qquad \text{Eqn. 4.}$$

Deviation score ranges from zero to one. By taking into account the relevance index (i.e., how good the given test is) and the disagreement index (i.e., how abnormal the patient's response is), the deviation score qualifies the relevance of a patient's test result. At step 44 technique 32 outputs a visualization of the deviation score corresponding to a given test, as described in more detail with respect to FIGS. 9-12.

Figure 5:
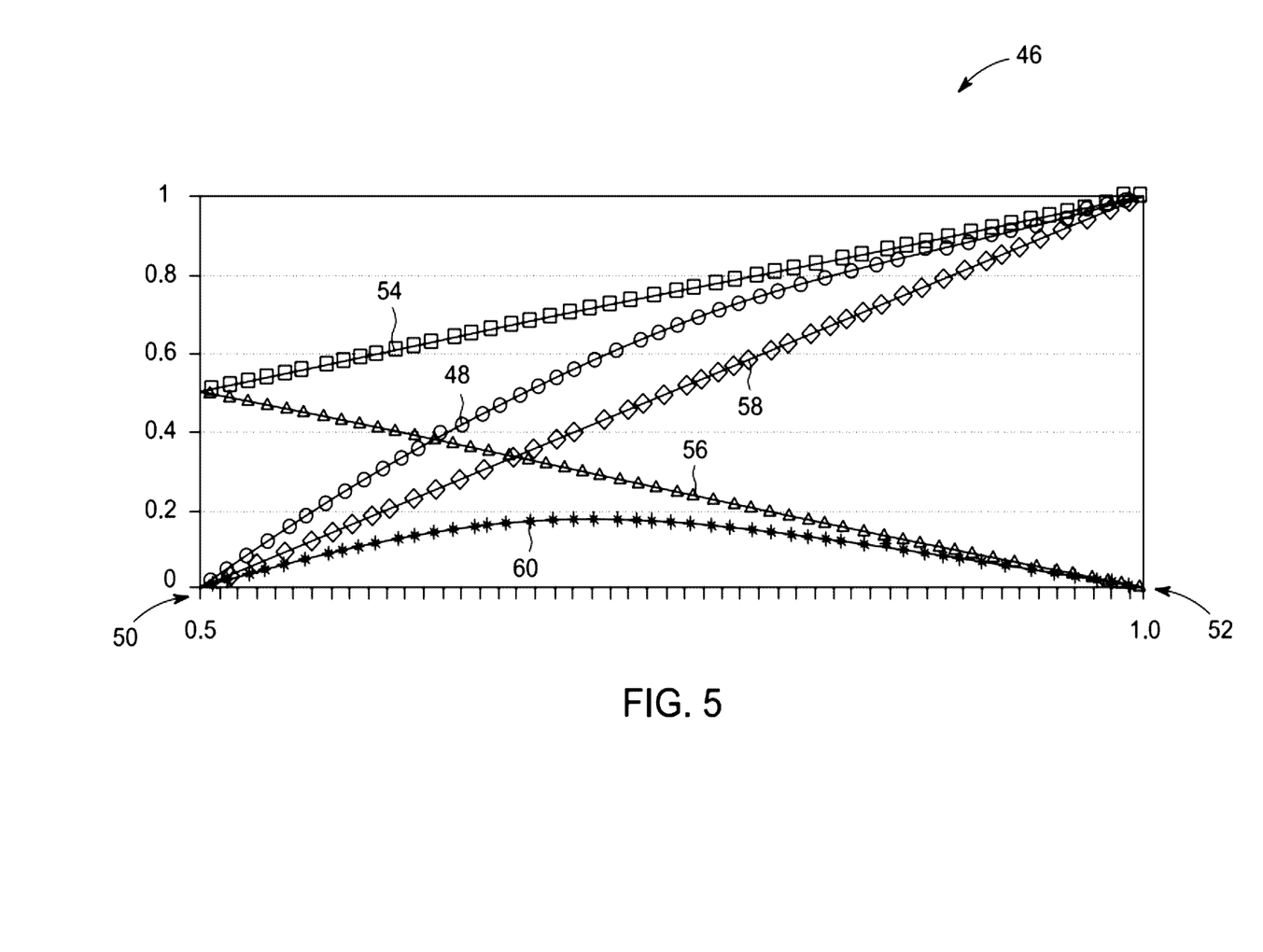
FIG. 5 is a graphical view representing the relationship between relative percentages, relevance indices, disagreement indices, and deviation scores for binary clinical data in accordance with an embodiment of the present invention.

FIG. 5 illustrates a graph 46 representing the relationship between the relevance index, disagreement index, and deviation score for exemplary binary tests having possible responses R1 and R2. Curve 48 represents the range of relevance indices for the tests. As shown, the x-axis ranges from a test 50 where the reference population has an even fifty-fifty split of responses between possible responses (R1, R2) to a test 52 where the entire reference population has the same response (R2). Because the reference population for test 50 is equally split between responses, the test provides no indication of whether a given result is normal or not for the reference population. Thus, test 50 is not useful for comparison with a patient response. Test 52, on the other hand, clearly defines the normal and abnormal response of the reference population for a test. Thus, test 52 is an ideal test for comparison to the patient response as an agreement between the patient response and the reference population guarantees that the patient's response is normal with respect to the reference population.

Curve 54 represents the disagreement index, DI(1), for a patient response of R1; curve 56 represents the disagreement index, DI(2), for a patient response of R2. Note that for test 50, DI(1) and DI(2) are both 0.5 because of the fifty-fifty split of the two, and RI=0. Moving left to right along graph 46 from test 50 to test 52, DI(2) goes to zero while DI(1) and the relevance index both go to one. Deviation curve 58 represents the deviation score, DS(1), for a patient response of R1; deviation curve 60 represents the deviation score, DS(2), for a patient response of R2. DS(1) and DS(2) are both zero for test 50, indicating that test 50 is a bad test for reference purposes. DS(1) and DS(2) go to extremes for test 52, indicating that the patient's agreement or disagreement from the reference population is very meaningful.

Figure 6A:
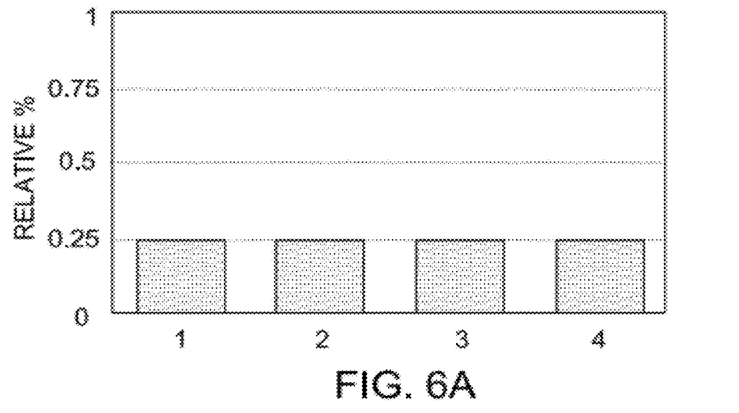
FIG. 6 illustrates relative percentages, disagreement indices, and deviation scores for an exemplary clinical dataset having four possible results.
Figure 6B:
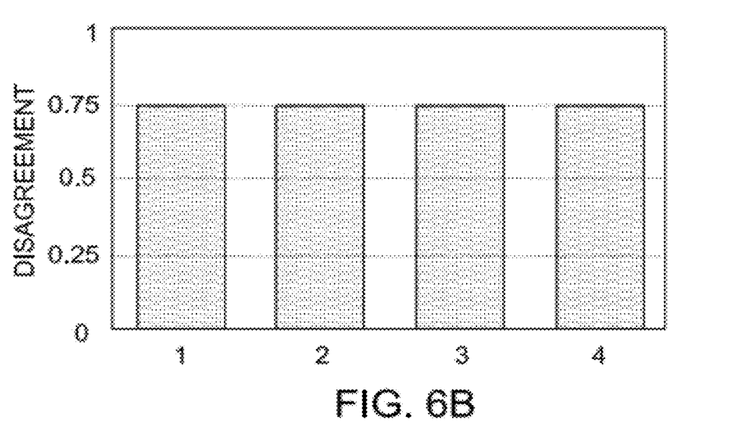
Figure 6C:
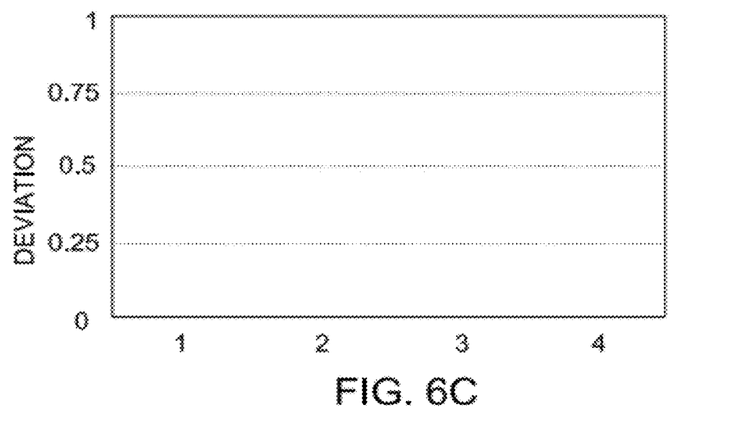

FIGS. 6(A-C), 7(A-C), and 8(A-C) illustrate the relationship between the relevance index, disagreement index, and deviation score for three exemplary tests, CASE 1, CASE 2, and CASE 3, each having four possible responses, R1, R2, R3, R4. CASES 1-3 provide exemplary illustrations of visualization technique 32 (FIG. 4) applied to a four bin test. However, one skilled in the art will recognize that technique 32 is equally applicable to tests having any number of discrete or finite responses.

In CASE 1 (FIG. 6), the responses of the reference population are evenly spread over the four bins (FIG. 6A). Therefore, the relevance index, RI, for CASE 1 is equal to zero. The disagreement index (FIG. 6B) is the same regardless of the patient response since relative probability for each bin is identical. The deviation score, DS, is zero regardless of the patient's response (FIG. 6C).

Figure 7A:
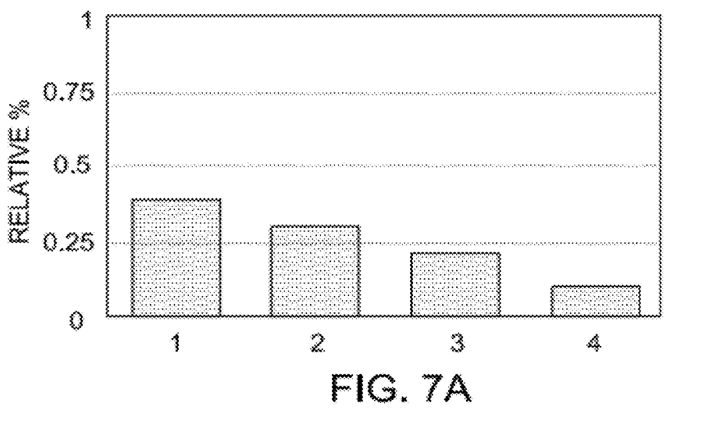
FIG. 7 illustrates relative percentages, disagreement indices, and deviation scores for another exemplary clinical dataset having four possible results.
Figure 7B:
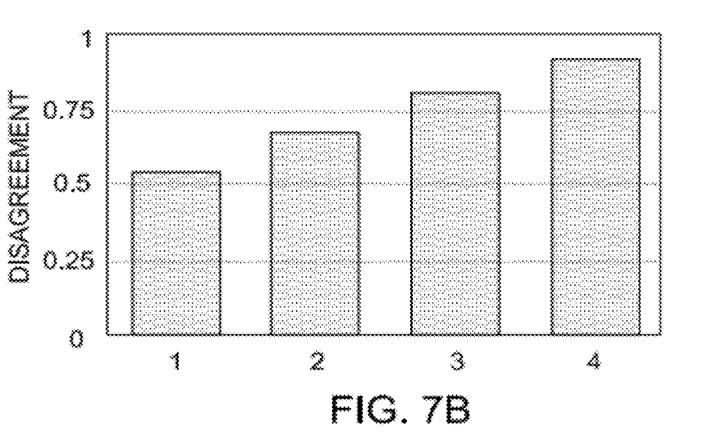
Figure 7C:
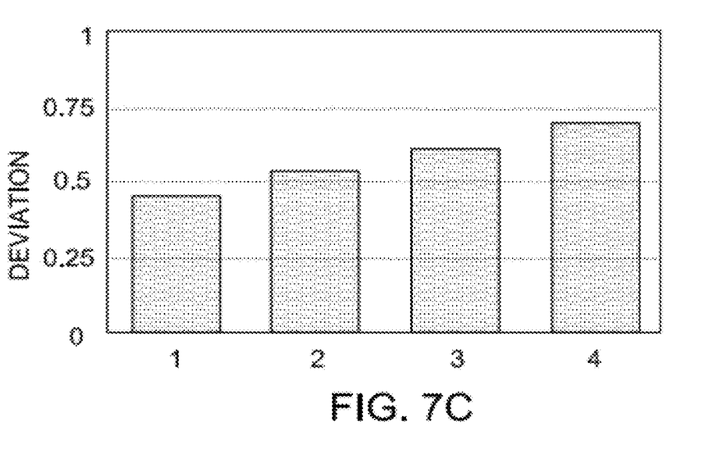

Referring now to CASE 2 (FIG. 7), the relative percentage of the reference population responses incrementally decrease by 0.1 between each bin (FIG. 7A). Accordingly, the disagreement index, DI, incrementally increases from bin 1 to bin 4 (FIG. 7B). The relevance index, RI, is 0.75 based on the difference in the number of patient responses between bin 1 and bin 4. The deviation score, DS, for CASE 2 is illustrated in FIG. 7C. Because the relative percentages of the reference population does not vary greatly between bins, the deviation score is relatively similar for each bin.

Figure 8A:
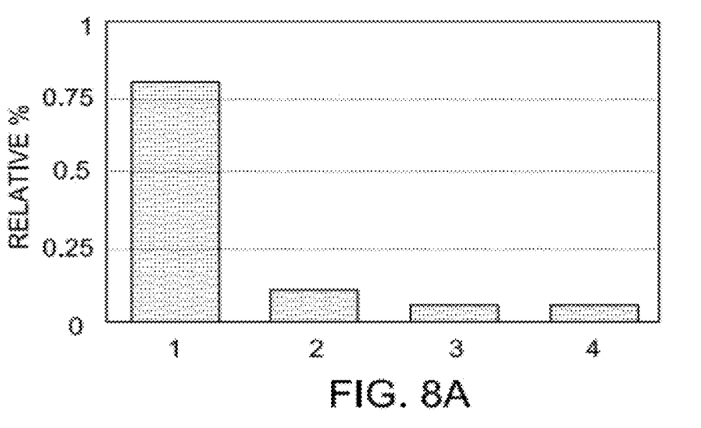
FIG. 8 illustrates relative percentages, disagreement indices, and deviation scores for another exemplary clinical dataset having four possible results.
Figure 8B:
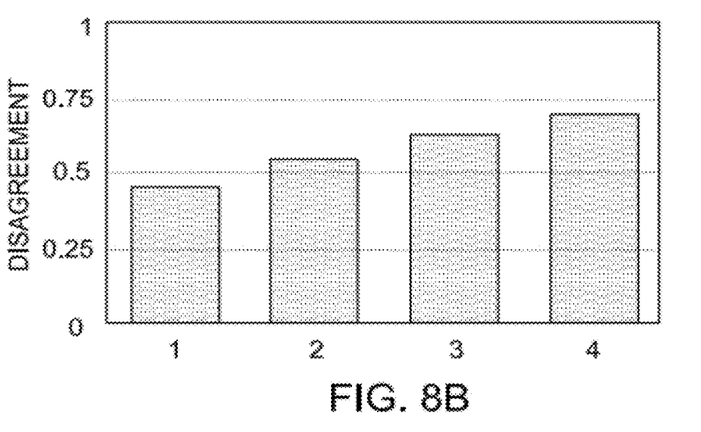
Figure 8C:
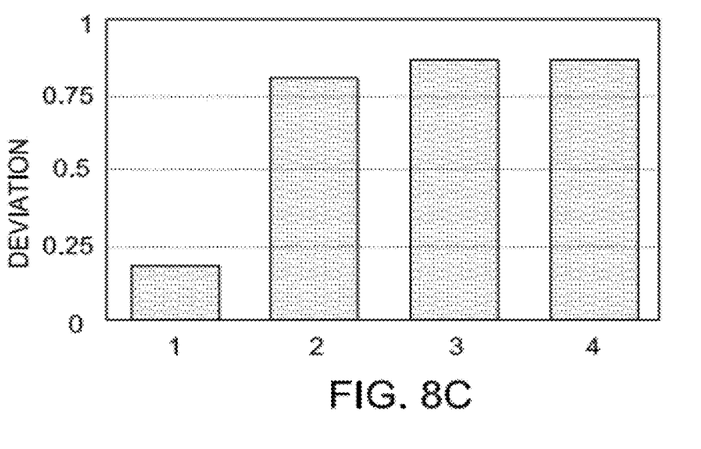

CASE 3 (FIG. 8) illustrates an example where the majority of the reference population fall within bin 1. In this case, the relative percentages for each bin are 0.8, 0.1, 0.05, and 0.05 for respective bins 1 through 4 (FIG. 8A). The relevance index for this test is 0.9375. As shown in FIG. 8C, any patient response other than one corresponding to bin 1 receives a very high deviation score.

When CASE 2 and CASE 3 are viewed together, the benefit of simultaneously accounting for the relevance of the test and the patient disagreement with the reference population is made clear. The relative percentage of the reference population in bin 4 of CASE 2 and bin 2 of CASE 3 are identical, thus the disagreement index for respective bins is also identical. However, the relevance index for CASE 3 is much higher than the relevance index for CASE 2. Thus, the test represented in CASE 3 is a better test for comparison with a patient response. Accordingly, the deviation score for bin 2 of CASE 3 is greater than the deviation score for bin 4 of CASE 2.

Figure 9:
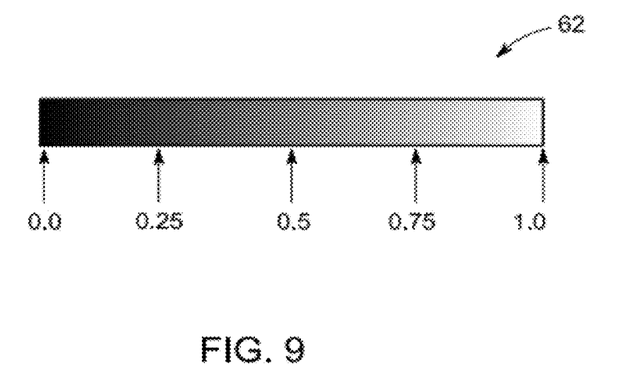
FIG. 9 illustrates a color scale for representing a disagreement score in accordance with one embodiment of the present invention.

Embodiments for visualizing the deviation score are illustrated in FIGS. 9-12. Referring first to FIG. 9, a color code is used to represent the deviation score, such as, for example, a continuous color scale 62. As shown, color scale 62 is a continuous scale ranging from black, representing a deviation score of 0, to white, representing a deviation score of 1. While color scale 62 is shown in black and white, color scale 62 may also be configured in color, such a red-green-blue scale that ranges from blue (DS=0) to red (DS=1), according to an alternative embodiment.

Figure 10:
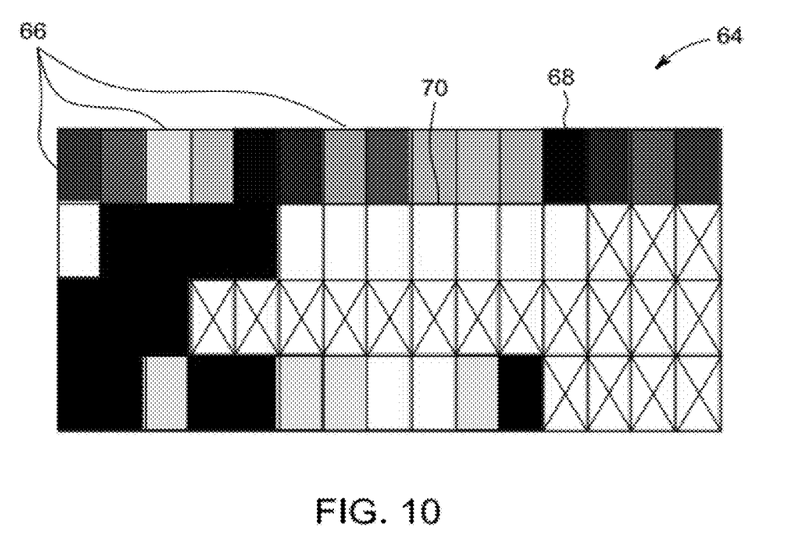
FIG. 10 is a graphical view representing agreement of the enumerated clinical data in Table 2 with a reference population incorporating the color scale of FIG. 9.

When all deviation scores for a series of patient tests are associated with the appropriate color from color scale 62, a visualization of the patient's test results is generated as a single representation based on the color-scaled deviation score. According to one embodiment, the visualization is grid 64 in a graphical user interface, the grid 64 having a number of cells 66 that correspond to a patient's response to different clinical tests, as shown in FIG. 10. Because all cells 66 are scaled using the same color scale, deviations between the patient test results and reference population are given meaning. For example, cell 68, which is assigned a color representing a deviation score close to zero, is easily differentiated from cell 70, which is assigned a color representing a deviation score close to one. Thus, a grid 64 allows a clinician to quickly recognize that the patient's response to the test corresponding to cell 68 was normal with respect to the reference population, while the patient's response to the test corresponding to cell 70 was abnormal.

Figure 11:
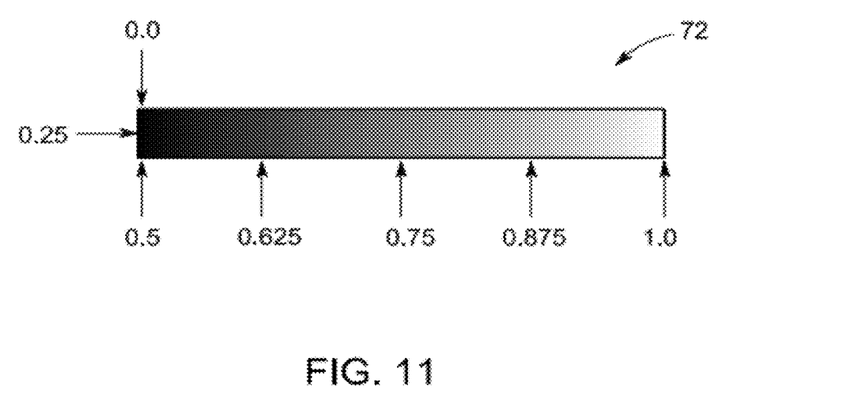
FIG. 11 illustrates a color scale for representing a disagreement score in accordance with another embodiment of the present invention.
Figure 12:
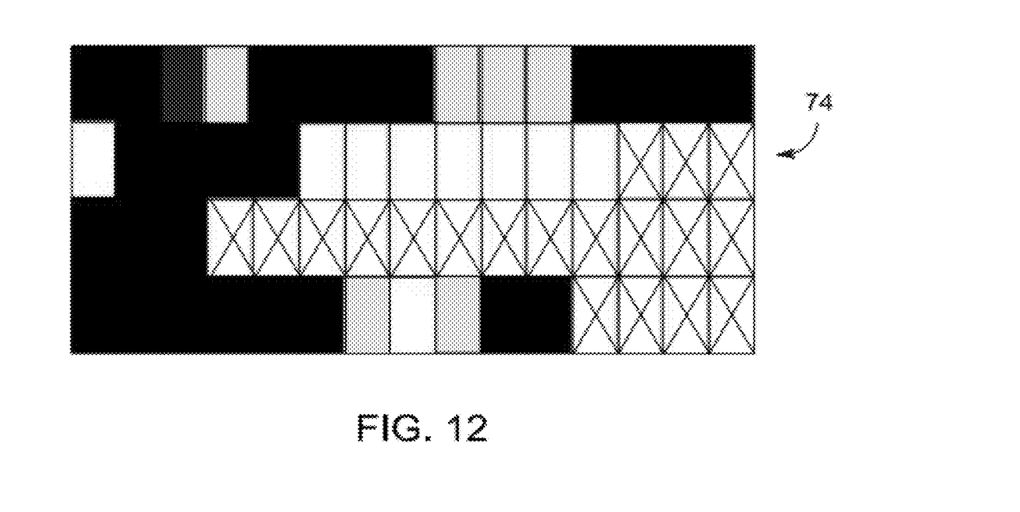
FIG. 12 is a graphical view representing agreement of the enumerated clinical data in Table 2 with a reference population incorporating the color scale of FIG. 11.

The color scale used to represent the deviation score may be configured according to user specifications. For example, a clinician may wish to configure the color scale to highlight a particular test result only when that test result is more likely abnormal than normal. Because all deviation scores are percentages between zero and one, a truncated color scale 72 ranging from 0.5 to 1 may be used to represent all deviation score values below 0.5 (e.g., values more likely normal than abnormal) as the color representing the lower end of the color scale, as shown in FIG. 11. Accordingly, truncated color scale 72 codes a deviation score of 0.5 to a first extreme of a color scale (e.g., black) and codes a deviation score of 1 to a second extreme of the color scale (e.g., white). Grid 74 (FIG. 12) illustrates the same patient data shown in FIG. 10 coded to correspond to color scale 72.

A technical contribution for the disclosed method and apparatus is that is provides for a computer implemented system and method of analyzing and visualizing enumerated clinical information.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, a system for analyzing clinical data includes a reference database having stored thereon a set of reference data comprising a plurality of enumerated results of a reference population for a clinical test and a patient database having stored thereon a set of clinical data corresponding to a patient result for the clinical test, wherein the patient result is selected from the plurality of enumerated results. The system also includes a processor programmed to access the patient database and the reference database, identify a distribution of the reference data over the plurality of enumerated test results, and calculate a relevance index based on the distribution of the reference data. The processor is further programmed to compare the patient result to the distribution of the reference data, calculate a disagreement index based on the comparison, and calculate a deviation index from the relevance index and the disagreement index. The system further includes a graphical user interface (GUI) configured to output a visualization of the deviation index to a user.

In accordance with another embodiment, a method includes accessing a first dataset comprising results from a clinical test having a plurality of possible outcomes corresponding thereto, the first dataset acquired from a reference population, calculating a reference index from the first dataset, the reference index representing a distribution of the first dataset over the plurality of possible outcomes, and accessing a second dataset comprising an outcome of the plurality of possible outcomes from the clinical test, the second dataset acquired from a patient of interest. The method also includes calculating a patient index from the second dataset, the patient index representing a disagreement between the patient outcome and the distribution of the first dataset, calculating a deviation score based on the reference index and the patient index, and outputting a visualization of the deviation score, the visualization depicting a relevance of the outcome of the second dataset.

In accordance with yet another embodiment, a computer readable storage medium has stored thereon a computer program comprising instructions, which, when executed by a computer, cause the computer to access a reference dataset comprising results of a reference population for a plurality of clinical tests, each clinical test having a finite number of possible results corresponding thereto. The instructions also cause the computer to access a patient dataset comprising results of a patient of interest for the plurality of clinical tests, the results of the patient of interest selected from the finite number of possible results and calculate a plurality of relevance indices from the reference dataset for the plurality of clinical tests, each of the plurality of relevance indices representing a distribution of the reference dataset for a respective clinical test. Further, the instructions cause the computer to calculate a plurality of disagreement indices, each of the plurality of disagreement indices representing a disagreement between the patient dataset and the reference dataset for a respective clinical test, calculate a plurality of deviation scores based on the plurality of relevance indices and the plurality of disagreement indices, and output a graphical display of the plurality of deviation scores, the graphical display depicting a relevance of the results of the patient of interest with respect to the reference population.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for analyzing clinical data comprising:
   a reference database having stored thereon a set of reference data comprising a plurality of enumerated results of a reference population for a clinical test;
   a patient database having stored thereon a set of clinical data corresponding to a patient result for the clinical test, wherein the patient result is selected from the plurality of enumerated results;
   a processor programmed to:
   access the patient database and the reference database;
   identify a distribution of the reference data over the plurality of enumerated test results;
   calculate a relevance index based on the distribution of the reference data;
   compare the patient result to the distribution of the reference data;
   calculate a disagreement index based on the comparison; and calculate a deviation index from the relevance index and the disagreement index; and a graphical user interface (GUI) configured to output a visualization of the deviation index to a user.

2. The system of claim 1 wherein the set of reference data and the set of clinical data comprise data from a binary test.

3. The system of claim 1 wherein the processor is further programmed to:

generate a continuous scale corresponding to the deviation index; and code the deviation index using the continuous scale.

4. The system of claim 3 wherein the GUI is further configured to display the coded deviation index.

5. The system of claim 1 wherein the processor is further programmed to:

identify an enumerated result of the plurality of enumerated results having a lowest relative percentage;

identify an enumerated result of the plurality of enumerated results having a highest relative percentage; and calculate the relevance index using the enumerated results having the lowest and highest relative percentages.

6. The system of claim 1 wherein the processor is further programmed to:

identify a relative percentage ($P_i$) of the reference population corresponding to the patient result;

calculate the disagreement index (DI) according to:

$$DI=(1-P_i).$$

7. The system of claim 1 wherein the reference database comprises data acquired from a population of normals for the clinical test.

8. A method comprising:

accessing a first dataset comprising results from a clinical test having a plurality of possible outcomes corresponding thereto, the first dataset acquired from a reference population;

calculating a reference index from the first dataset, the reference index representing a distribution of the first dataset over the plurality of possible outcomes;

accessing a second dataset comprising a patient outcome of the plurality of possible outcomes from the clinical test, the second dataset acquired from a patient of interest;

calculating a patient index from the second dataset, the patient index representing a disagreement between the patient outcome and the distribution of the first dataset;

calculating a deviation score based on the reference index and the patient index; and outputting a visualization of the deviation score, the visualization depicting a relevance of the patient outcome of the second dataset.

9. The method of claim 8 wherein calculating the reference index comprises calculating a relative percentage of each of the plurality of possible outcomes of the clinical test for the results of the first dataset.

10. The method of claim 9 further comprising:

identifying an outcome of the plurality of possible outcomes having a lowest relative percentage;

identifying an outcome of the plurality of possible outcomes having a highest relative percentage; and defining the reference index based on the highest relative percentage and the lowest relative percentage.

11. The method of claim 9 wherein calculating the patient index comprises identifying the relative percentage of the outcome calculated from the first dataset corresponding to the patient outcome.

12. The method of claim 11 comprising calculating the patient index (DI) according to:

$$DI=(1-P_i)$$

where $P_i$ represents the relative percentage of the outcome calculated from the first dataset corresponding to the patient outcome.

13. The method of claim 8 further comprising defining a continuous color scale to represent the deviation score.

14. A non-transitory computer readable storage medium having stored thereon a computer program comprising instructions, which, when executed by a computer, cause the computer to:

access a reference dataset comprising results of a reference population for a plurality of clinical tests, each clinical test having a finite number of possible results corresponding thereto;

access a patient dataset comprising results of a patient of interest for the plurality of clinical tests, the results of the patient of interest selected from the finite number of possible results;

calculate a plurality of relevance indices from the reference dataset for the plurality of clinical tests, each of the plurality of relevance indices representing a distribution of the reference dataset for a respective clinical test;

calculate a plurality of disagreement indices, each of the plurality of disagreement indices representing a disagreement between the patient dataset and the reference dataset for a respective clinical test;

calculate a plurality of deviation scores based on the plurality of relevance indices and the plurality of disagreement indices; and output a graphical display of the plurality of deviation scores, the graphical display depicting a relevance of the results of the patient of interest with respect to the reference population.

15. The computer readable storage medium of claim 14 wherein the instructions further cause the computer to:

identify a least probable outcome from the reference dataset for each of the plurality of clinical tests; and identify a most probable outcome from the reference dataset for each of the plurality of clinical tests.

16. The computer readable storage medium of claim 14 wherein the instructions further cause the computer to:

generate a color scale for the graphical display; and apply the color scale to the plurality of deviation scores.

17. The computer readable storage medium of claim 14 wherein the instructions further cause the computer to output the graphical display of the plurality of deviation scores on a common display.

18. The computer readable storage medium of claim 14 wherein the instructions further cause the computer to:

identify a relative percentage of the reference population corresponding to each of the finite number of possible results for the plurality of clinical tests; and identify the relative percentage of the reference population corresponding to the results of the patient of interest.

19. The computer readable storage medium of claim 14 wherein the instructions further cause the computer to calculate the plurality of relevance indices such that a relevance index equal to zero represents an irrelevant test and a relevance index equal to one represents a relevant test.

20. The computer readable storage medium of claim 14 wherein the instructions further cause the computer to calculate the plurality of disagreement indices such that a disagreement index equal to zero represents a normal test result and a disagreement index equal to one represents an abnormal test result.

\* \* \* \* \*